(12) United States Patent
Kawashima

(10) Patent No.: US 7,013,701 B2
(45) Date of Patent: Mar. 21, 2006

(54) INSPECTION METHOD OF MULTILAYER GAS SENSING DEVICE

(75) Inventor: Yukio Kawashima, Yokkaichi (JP)

(73) Assignee: Denso Corporation, (JP)

( * ) Notice: Subject to any disclaimer, the term of this patent is extended or adjusted under 35 U.S.C. 154(b) by 181 days.

(21) Appl. No.: 10/730,884

(22) Filed: Dec. 10, 2003

(65) Prior Publication Data

US 2004/0123642 A1    Jul. 1, 2004

(30) Foreign Application Priority Data

Dec. 13, 2002   (JP) ............................. 2002-362796

(51) Int. Cl.
*G01M 3/00*    (2006.01)
(52) U.S. Cl. ..................................... 73/1.06; 324/551
(58) Field of Classification Search ................. 73/1.06, 73/118.1; 324/500, 537, 734, 551, 554, 693, 324/557
See application file for complete search history.

(56) References Cited

U.S. PATENT DOCUMENTS 5,419,828 A    5/1995    Nakano et al.
5,969,532 A *  10/1999   Usui et al. ................... 324/557
6,566,887 B1 * 5/2003    Smith et al. ................. 324/514

FOREIGN PATENT DOCUMENTS

JP    7-120429    5/1995

* cited by examiner

Primary Examiner—Robert Raevis
(74) Attorney, Agent, or Firm—Nixon & Vanderhye PC

(57) ABSTRACT

Provided is an inspection method for a multilayer gas sensing device, capable of certainly and easily detecting a defective product originating from faults such as gaps or cracks. For the inspection of the gas sensing device including a sensor cell in which a measured gas side electrode is coated with a porous diffusion resistance layer in a stacked condition and the diffusion resistance layer is further coated with a dense protective layer in a stacked condition, in a state where the gas sensing device is immersed in a conductive inspection solution and a reference electrode of the sensor cell is placed into a non-contact with the solution, a voltage is applied between the solution and the reference electrode to measure a current flowing therebetween. On the basis of the measured current value, a decision is made as to whether or not the insulation is kept between the solution and the reference electrode.

5 Claims, 8 Drawing Sheets

INSPECTION METHOD OF MULTILAYER GAS SENSING DEVICE

BACKGROUND OF THE INVENTION

1) Field of the Invention

The present invention relates to an inspection method for a multilayer gas sensing device installed in an exhaust system of an internal combustion engine for combustion control.

2) Description of the Related Art

The following multilayer type device has been known as a multilayer gas sensing device to be provided in an exhaust system of an engine of a vehicle to measure the concentrations of various gases contained in an exhaust gas, with the measurement results being used for engine combustion control or the like.

As shown in FIG. 11, this multilayer gas sensing device, generally designated at reference numeral 1, is made up of a solid electrolyte plate 11 carrying a measured gas side electrode 121 exposed to a measured gas (gas to be measured) and a reference electrode 131 confronting a reference gas chamber 150 and exposed to a reference gas, a spacer 15 for defining the reference gas chamber 150 and a heater substrate 191 (which will be described later).

In this multilayer gas sensing device 1, the measured gas side electrode 121 is covered with a porous diffusion resistance layer 141, and a dense protective layer 144 capable of substantially cutting off gases is provided to surround the overall circumference of the multilayer gas sensing device 1.

Meanwhile, a multilayer gas sensing device is produced by properly stacking green sheets forming a solid electrolyte plate, a spacer and others and calcining the resultant stack. Therefore, if the adherence between the green sheets is insufficient, off-specification products can develop. Moreover, there is a possibility of the occurrence of cracking in the green sheets, the electrodes and others. For searching these defectives, a conventional technique has employed a staining inspection.

However, in the case of the staining inspection, if the staining solution do not soak sufficiently into adherence-insufficient portions or cracking portions, difficulty is experienced in detecting troubles.

In addition, since the multilayer gas sensing device constructed as mentioned above is covered with a dense protective layer throughout its overall circumference, the staining solution soakage insufficiency occurs in the adherence-insufficient portions or the cracking portions, which makes it very difficult to find the defective products.

Still additionally, for example, in the case of the constructions shown in FIGS. 3 and 4 other than the construction shown in FIG. 11 which have a dense protective layer formed on the surface of the multilayer gas sensing device, likewise, the staining solution soakage insufficiency occurs, which makes it very difficult to find the defective products.

SUMMARY OF THE INVENTION

The present invention has been developed with a view to eliminating such a problem, and it is therefore an object of the invention to provide an inspection method for a multilayer gas sensing device which is capable of certainly and easily finding defectives stemming from faults such as gaps (crevices) and cracks.

For this purpose, in accordance with an aspect of the present invention, there is provided an inspection method for a multilayer gas sensing device which comprises a sensor cell including a solid electrolyte plate, a measured gas side electrode placed on a surface of the solid electrolyte plate to be exposed to a measured gas and a reference electrode placed on a surface of the solid electrolyte plate to be exposed to a reference gas, with the measured gas side electrode being coated with a porous diffusion resistance layer in a stacked condition and the diffusion resistance layer being further coated with a dense protective layer in a stacked condition, wherein, in a state where the multilayer gas sensing device is immersed in a conductive inspection solution (liquid) while the reference electrode is not brought into contact with the conductive inspection solution, a voltage is applied between the conductive inspection solution and the reference electrode to measure a current flowing between the conductive inspection solution and the reference electrode so that a decision is made as to whether or not the insulation is kept between the conductive inspection solution and the reference electrode.

The effects of the present invention are as follows.

In the inspection method according to the present invention, the multilayer gas sensing device is immersed in a conductive inspection solution and a voltage is applied between the conductive inspection solution and the reference electrode to make a decision as to whether or not the insulation is kept therebetween, thereby detecting the non-defective/defective of the multilayer gas sensing device.

Meanwhile, the multilayer gas sensing device is made such that a voltage is applied between a measured gas side electrode in a sensor cell and a reference gas side electrode to ionize oxygen in a measured gas so that an oxygen concentration is measured on the basis of an oxygen ion current occurring from the oxygen ions.

Alternatively, a potential difference between the measured gas side electrode and the reference electrode is measured on the basis of a concentration difference on a specific gas between a measured gas and a reference gas to measure the concentration of the specific gas on the basis of the measured potential difference.

Still alternatively, a voltage is applied between the measured gas side electrode in the sensor cell and the reference gas side electrode to decompose a specific gas in a measured gas to producing oxygen ions so that the concentration of the specific gas is measured on the basis of an oxygen ion current occurring therefrom.

Accordingly, the reference electrode exposed to the reference gas is required to be placed into a cutoff condition from a measured gas and, hence, the multilayer gas sensing device is required to have a construction capable of the cutoff from the measured gas.

In the inspection method according to the present invention, if a current flows between the reference electrode and the conductive inspection solution existing around the multilayer gas sensing device, it can be considered that gaps, cracks or the like exist anywhere in the multilayer gas sensing device and the conductive inspection solution flows into the interior of the multilayer gas sensing device so that the electrical conduction occurs between the conductive inspection solution and the reference electrode.

In a case in which the conductive inspection solution and the reference voltage are in a substantially insulating condition, it can be considered that the conductive inspection solution barely flows into the interior of the multilayer gas sensing device and faults such as gaps or cracks barely exist in the multilayer gas sensing device.

Moreover, unlike the conventional method of making a staining solution soak into the multilayer gas sensing device to find the faults through the visual inspection, the inspection method according to the present invention can find the defectives stemming from the faults at portions in which the staining solution is hard to soak.

Still moreover, since the decision on defectives is made on the basis of a current flowing between the conductive inspection solution and the reference electrode, the state of the fault can easily be digitized and the decision can automatically be realized at a low cost without requiring a high-priced image recognition system and depending on the visual confirmation by an operator.

Accordingly, the present invention can provide a multilayer gas sensing device inspection method capable of certainly and easily detecting defectives due to faults such as gaps or cracks.

Furthermore, the inspection method according to the present invention is generally applicable to multilayer gas sensing devices and, in particular, it is optically applicable to a multilayer gas sensing device having a dense protective layer in which a staining solution is hard to soak.

In addition, among the multilayer gas sensing devices, there are a one-cell type oxygen sensor element (limiting current type, oxygen concentration electromotive-force type) for detecting an oxygen concentration, an air-fuel ratio sensor element for detecting an air-fuel ratio by measuring an oxygen concentration in an exhaust system of an internal combustion engine such as a car engine, a λ sensor element for detecting a theoretical air-fuel ratio (λ point) therein, two-cell type NOx sensor element, a CO sensor element, an HC sensor element, and other elements.

In the present invention, when a voltage is applied between the conductive inspection solution and the reference electrode, it is preferable that the voltage is applied between a reference side external terminal, which is electrically connected to the reference electrode and formed in an exposed state in the exterior of the multilayer gas sensing device and which does not come into contact with the conductive inspection solution, and the conductive inspection solution.

This can eliminate the need for equipment extending to the reference electrode in the interior of the multilayer gas sensing device for the application of a voltage and, hence, can facilitate the voltage application.

In addition, preferably, the voltage to be applied between the conductive inspection solution and the reference electrode is in a range from 250V to 1000V.

This can efficiently distinguish the defectives at a low cost without damaging the multilayer gas sensing device.

When the voltage to be applied exceeds 1000V, there is a possibility of the multilayer gas sensing device being damaged, and the application of a high voltage makes it difficult to ensure the safety, and increases the power dissipation and the cost.

On the other hand, when the voltage does not reach 250V, the current flowing therein becomes too small to easily find the defectives.

Still additionally, taking into consideration a load to be applied to the power supply equipment for the inspection and the efficiency of the detection of defectives, it is preferable that the voltage to be applied therebetween is in a range from 490V to 510V.

Yet additionally, preferably, when a current flowing between the conductive inspection solution and the reference electrode in response to the voltage application therebetween is below 5 $\mu$A, the multilayer gas sensing device is decided to be a non-defective product.

This enhances the reliability of this inspection method and shortens the inspection time. If it exceeds 5 $\mu$A, the accuracy (detection ability) of the decision on the non-defective/defective can lower.

Moreover, preferably, the conductive inspection solution is an ethanol (ethyl alcohol).

Preferably, the conductive inspection solution employable in the present invention is made of a material which not only has a conductive property in some degree but also has a high soakage with respect to faults such as cracks and even does not deteriorate/contaminate the multilayer gas sensing device. A material satisfying these requirements is an ethanol.

It is also acceptable to use pure water or a mixture of pure water and ethanol, and further to use an alcohol similar in property to the ethanol without problems.

BRIEF DESCRIPTION OF THE DRAWINGS

Other objects and features of the present invention will become more readily apparent from the following detailed description of the preferred embodiments taken in conjunction with the accompanying drawings in which.

DESCRIPTION OF THE PREFERRED EMBODIMENTS

Embodiments of the present invention will be described hereinbelow with reference to the drawings.

(First Embodiment)

Figure 3:
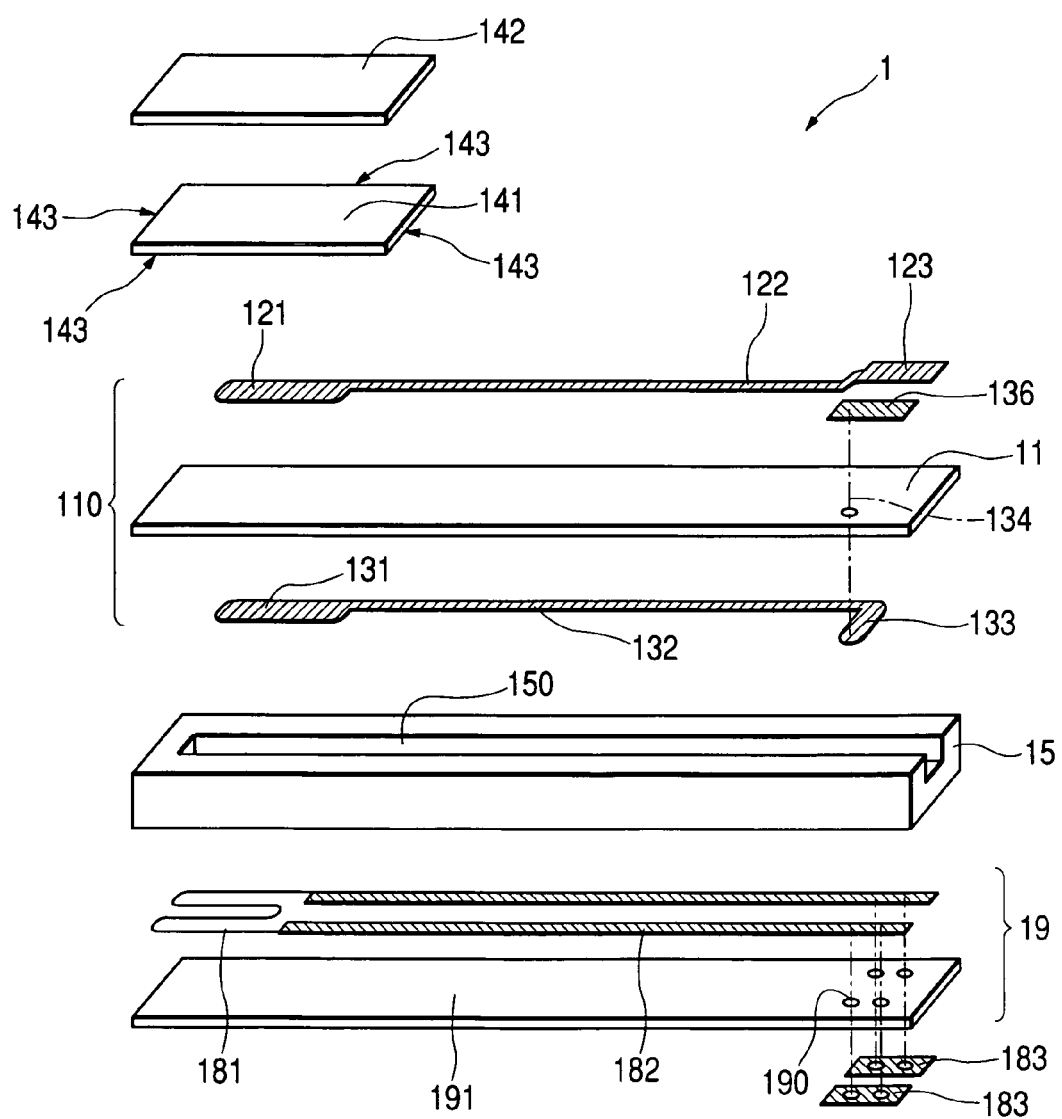
FIG. 3 is an exploded view showing the multilayer gas sensing device according to the first embodiment.
Figure 4:
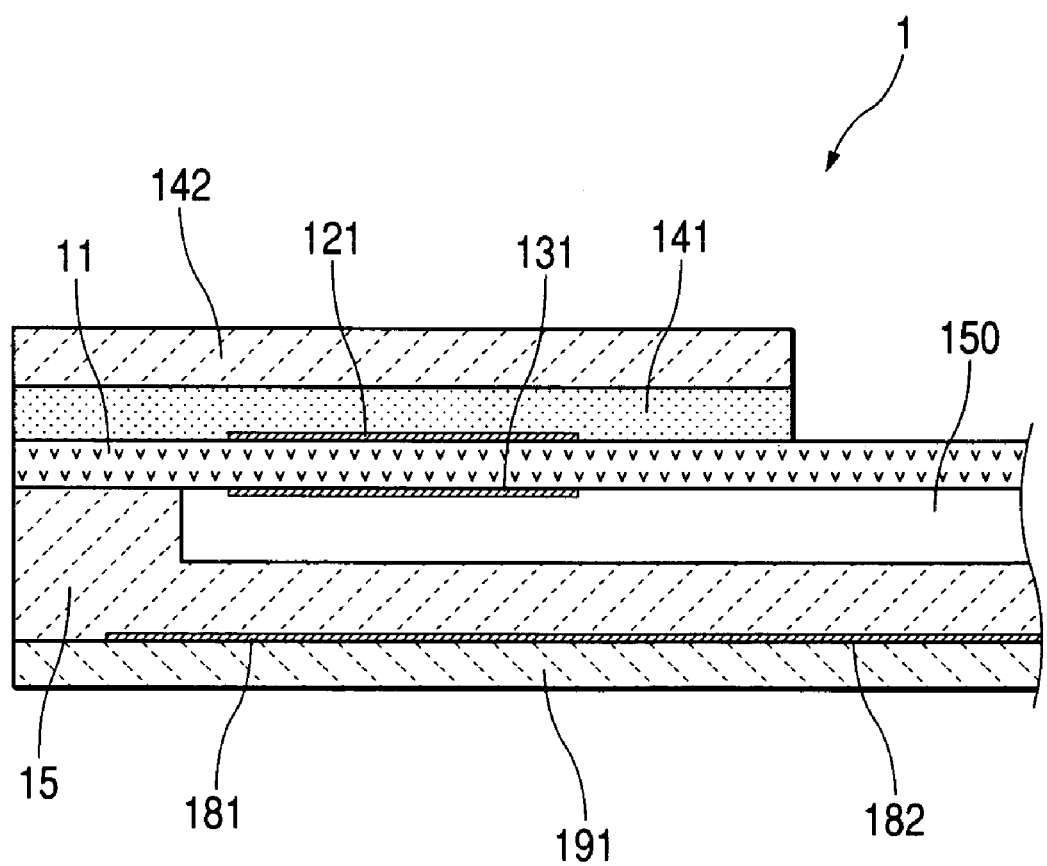
FIG. 4 is an illustration of an essential part of the multilayer gas sensing device according to the first embodiment.

A first embodiment of the present invention relates to an inspection method of inspecting a multilayer gas sensing device designated at reference numeral 1 in FIGS. 3 and 4.

The multilayer gas sensing device 1 comprises a sensor cell 110 including a solid electrolyte plate 11, a measured gas side electrode 121 placed on a surface of the solid electrolyte plate 11 to be exposed to a gas to be measured (measured gas) and a reference electrode 131 placed on a surface of the solid electrolyte plate 11 to be exposed to a reference gas, with the measured gas side electrode 121 being coated with a porous diffusion resistance layer 141 in a stacked condition and the porous diffusion resistance layer 141 being further coated with a dense protective layer 142 in a stacked condition.

Figure 1:
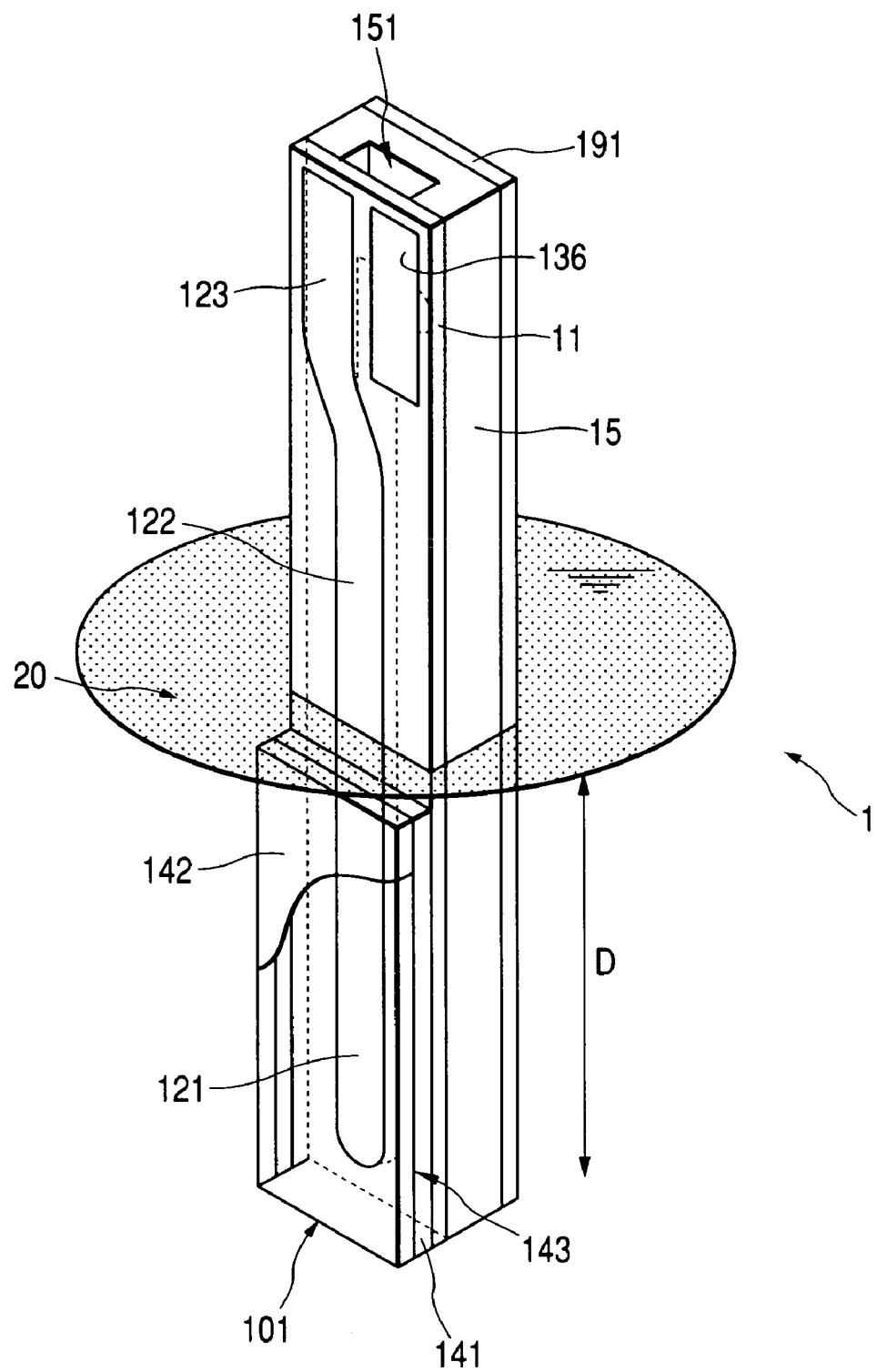
FIG. 1 is an illustration useful for explaining the inspection of a multilayer gas sensing device according to a first embodiment of the present invention.
Figure 2:
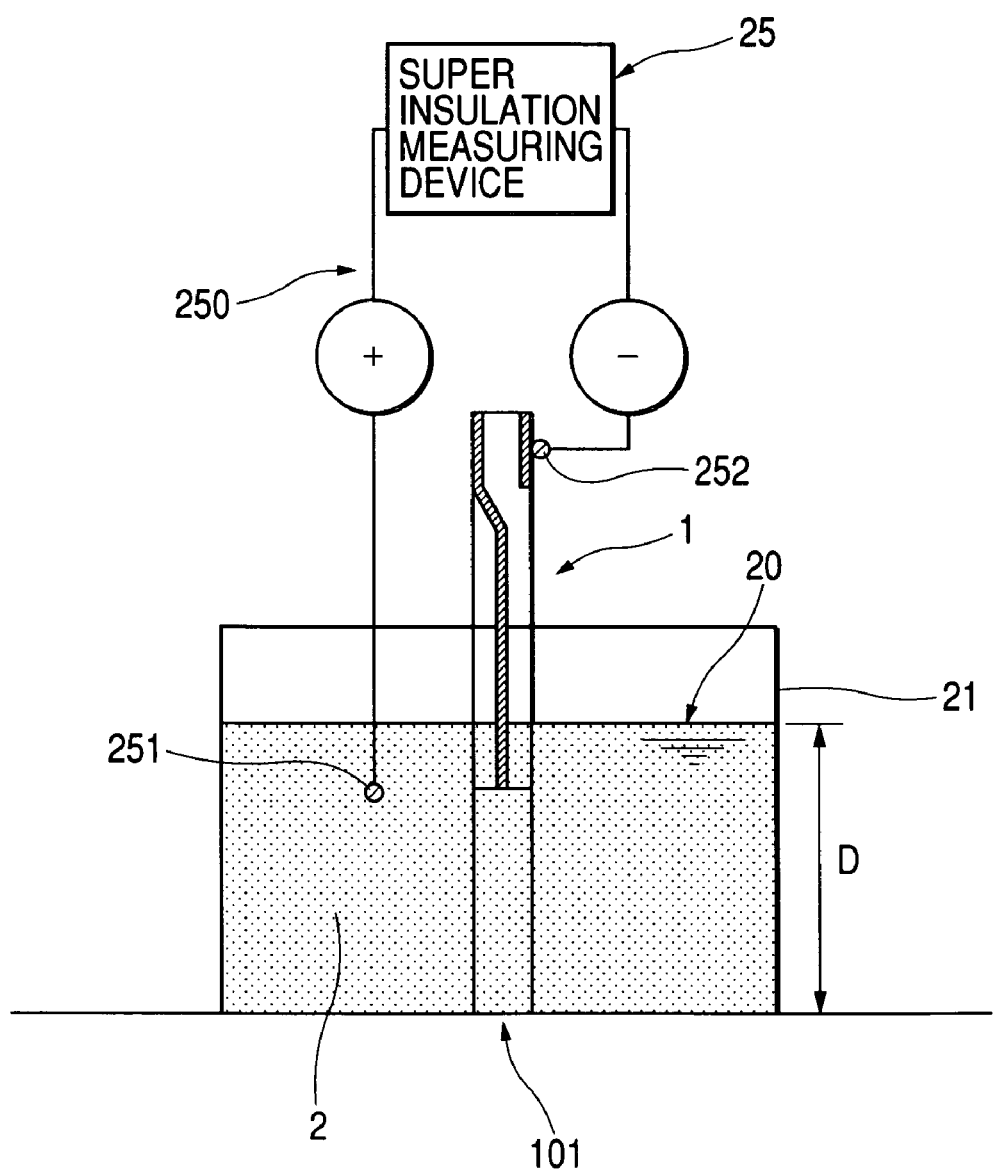
FIG. 2 is an illustration useful for explaining the inspection of the multilayer gas sensing device according to the first embodiment.

That is, as shown in FIGS. 1 and 2, the aforesaid multilayer gas sensing device 1 is immersed in a conductive inspection solution 2, and the aforesaid reference electrode 131 is placed into non-contact with the conductive inspection solution 2. In this state, a voltage is applied between the conductive inspection solution 2 and the reference electrode 131 to measure a current flowing between the conductive inspection solution and the reference electrode 131, thereby making a decision as to whether or not the insulation is kept between the conductive inspection solution 2 and the reference electrode 131.

A description will be given hereinbelow of the multilayer gas sensing device 1 to be inspected according to this embodiment.

The multilayer gas sensing device 1 is of a limiting current type made to measure a concentration of oxygen contained in a measured gas.

As shown in FIGS. 3 and 4, the multilayer gas sensing device 1 is constructed by stacking the solid electrolyte plate 11, a spacer 15 for the formation of a reference gas chamber and a heater 19, and includes the measured gas side electrode 121 on one surface of the solid electrolyte plate 11, and a lead portion 122 and an external terminal 123 electrically connected to this electrode 121.

The measured gas side electrode 121 is coated with the porous diffusion resistance layer 141 having a gas permeability, and the diffusion resistance layer 141 is coated with a dense protective layer 142 hardly having the gas permeability. On the other hand, side surfaces 143 of the diffusion resistance layer 141 are not coated with the dense protective layer 142 and, hence, the measured gas is introduced through the side surfaces 143 into the vicinity of the measured gas side electrode 121.

The other surface of the solid electrolyte plate 11 carries the reference electrode 131, and a lead portion 132 and an internal terminal 133 electrically connected to this electrode 131. The internal terminal 133 is electrically connected through a through hole 134 to a reference side external terminal 136 adjacent to the external terminal 123.

The reference electrode 131 confronts a reference gas chamber 150 defined by the spacer 15 and is exposed to a reference gas.

The spacer 15 has a column-like configuration including a groove portion, and this groove portion establishes the reference gas chamber 150 in cooperation with the solid electrolyte plate 11. The reference gas chamber 150 is isolated from the measured gas atmosphere, and the atmospheric air is introduced thereinto through an opening portion 151.

The aforesaid heater 19 is composed of a heater substrate, a heating element 181 placed on the heater substrate to generate heat when energized, heater lead portions 182 electrically connected to the heating element 181, and heater terminals 183 located on a surface of the heater substrate 191 opposite to the heating element 181 mounted side and exposed to the exterior of the multilayer gas sensing device 1.

Incidentally, it is also possible that, although not shown, another layer is put between the heater substrate 191 and the spacer 15, between the spacer 15 and the solid electrolyte plate 11, between the solid electrolyte plate 11 and the diffusion resistance layer 141, and between the diffusion resistance layer 141 and the dense protective layer 142.

A detailed description will be given hereinbelow of an inspection method for the multilayer gas sensing device 1 according to this embodiment.

As shown in FIGS. 1 and 2, the multilayer gas sensing device 1 is put in the conductive inspection solution 2 having a depth which is the degree to which the dense protective layer 142 and the diffusion resistance layer 141 are immersed therein. At this time, the external terminal 123 and the reference side external terminal 136 are exposed to the atmosphere in the exterior of the conductive inspection solution 2, and the opening portion 151 of the reference gas chamber 150 is also exposed to the external atmosphere so that the atmospheric air can freely get in and out of the reference gas chamber 150. In FIG. 2, reference numeral 21 designates an inspection vessel accommodating the conductive inspection solution 2.

In this embodiment, the depth (distance) D from the tip portion 101 of the multilayer gas sensing device 1 up to a liquid level 20 is set at D=18 to 30 mm.

The possible faults of the multilayer gas sensing device 1 are as follows. That is, (1) cracks occurring in the measured gas side electrode 121 or the reference electrode 131, and cracks occurring in the solid electrolyte plate 11 carrying the electrodes 121 and 131;

(2) cracks occurring in the lead portions 122, 132, the internal terminal 133, the external terminal 123 and the reference side external terminal 136;

(3) gaps (crevices) occurring between the dense protective layer 142 and the diffusion resistance layer 141 due to poor adherence or the like;

(4) gaps occurring between the diffusion resistance layer 141 and the solid electrolyte plate 11 due to poor adherence or the like; and (5) gaps occurring between the solid electrolyte plate 11 and the spacer 15 due to poor adherence or the like.

Of (1) to (5), in the case of (1) "cracks occurring in the measured gas side electrode 121 or the reference electrode 131, and cracks occurring in the solid electrolyte plate 11 carrying the electrodes 121 and 131", difficulty is encountered in making a staining solution soak thereinto because of the presence of the dense protective layer 142, and the stained sites are hard to confirm through the visual inspection. Therefore, to a conventional staining method, these faults are hard to confirm.

According to this embodiment, as shown in FIG. 2, an inspection circuit 250 including a super insulation measuring device 25 is connected between a ground electrode 251 immersed in the conductive inspection solution 2 and an electrode 252 brought into contact with the reference side external terminal 136 of the multilayer gas sensing device 1, and a voltage of 500V is applied therebetween to measure the insulation states thereof. In this case, for the selection between non-defectives and defectives, the device 1 is handled as a non-defective product when a current below 5 $\mu$A flows therebetween, while the device 1 is handled as a defective product when a current exceeding 5 $\mu$A flows therebetween.

A comparison was made between the inspection method according to this embodiment and a conventional staining method.

For the inspection method according to this embodiment, 10 multilayer gas sensing devices 1 shown in FIGS. 3 and 4 were inspected, and the inspection result showed that non-defective products were 5 in number and the defective products were 5 in number. Both the non-defective products and the defective products were actually mounted in an exhaust system of an actual vehicle engine in a state built in a gas sensor to measure an oxygen concentration in an exhaust gas. In consequence, the five multilayer gas sensing devices handled as non-defective products through the inspection method according to this embodiment could measure the oxygen concentration normally, while the five multilayer gas sensing devices handled as defective products could not measure the oxygen concentration. This signifies that the inspection method according to this embodiment can certainly distinguish between the non-defective products and the defective products.

On the other hand, the inspection according to a staining solution soakage method (leaving for one minute) was made with respect to 10 multilayer gas sensing devices shown in FIGS. 3 and 4. The inspection result showed that the non-defective products were 9 in number and the defective products was 1 in number. Following this, likewise, both the non-defective products and the defective products were actually mounted in an exhaust system of an actual vehicle engine to measure an oxygen concentration in an exhaust gas. In consequence, four devices of the multilayer gas sensing devices handled as non-defective products generated an abnormal output. When the interiors of the devices which generated the abnormal output were examined through the decomposition cross-section observation, they involved the faults mentioned above in (1) to (5).

Thus, it was found that the inspection method according to this embodiment can more certainly find the multilayer gas sensing devices having the faults, as compared with the staining method.

In addition, a description will be given hereinbelow of the effects of this embodiment.

In a case in which a current flows between the reference electrode 131 and the conductive inspection solution 2 existing around the multilayer gas sensing device 1, it is considered that a gap, crack or the like lies anywhere in the multilayer gas sensing device 1 so that the conductive inspection solution 2 flows into the interior of the multilayer gas sensing device 1 to make an electrical connection between the conductive inspection solution 2 and the reference electrode 131.

In a case in which a substantially insulating condition exists between the conductive inspection solution 2 and the reference electrode 131, it is considered that the conductive inspection solution 2 hardly flows into the interior of the multilayer gas sensing device 1, that is, faults such as gaps or cracks barely reside in the multilayer gas sensing device 1.

In addition, the inspection method according to this embodiment can detect defective products stemming from faults existing at a portion where a staining solution is hard to enter, unlike a conventional method of making a staining solution soak thereinto to find faults through the visual observation.

Still additionally, since a decision on defective products is made on the basis of a current flowing between the conductive inspection solution 2 and the reference electrode 131, the state of the fault can easily be digitized and the decision can automatically be realized at a low cost without requiring a high-priced image recognition system and without depending on the visual confirmation by an operator.

Accordingly, the present invention can provide a multilayer gas sensing device inspection method capable of certainly and easily detecting defective products due to faults such as gaps or cracks.

(Second Embodiment)

A second embodiment of the present invention relates to an inspection apparatus for realizing the above-described inspection method according to the first embodiment.

Figure 5:
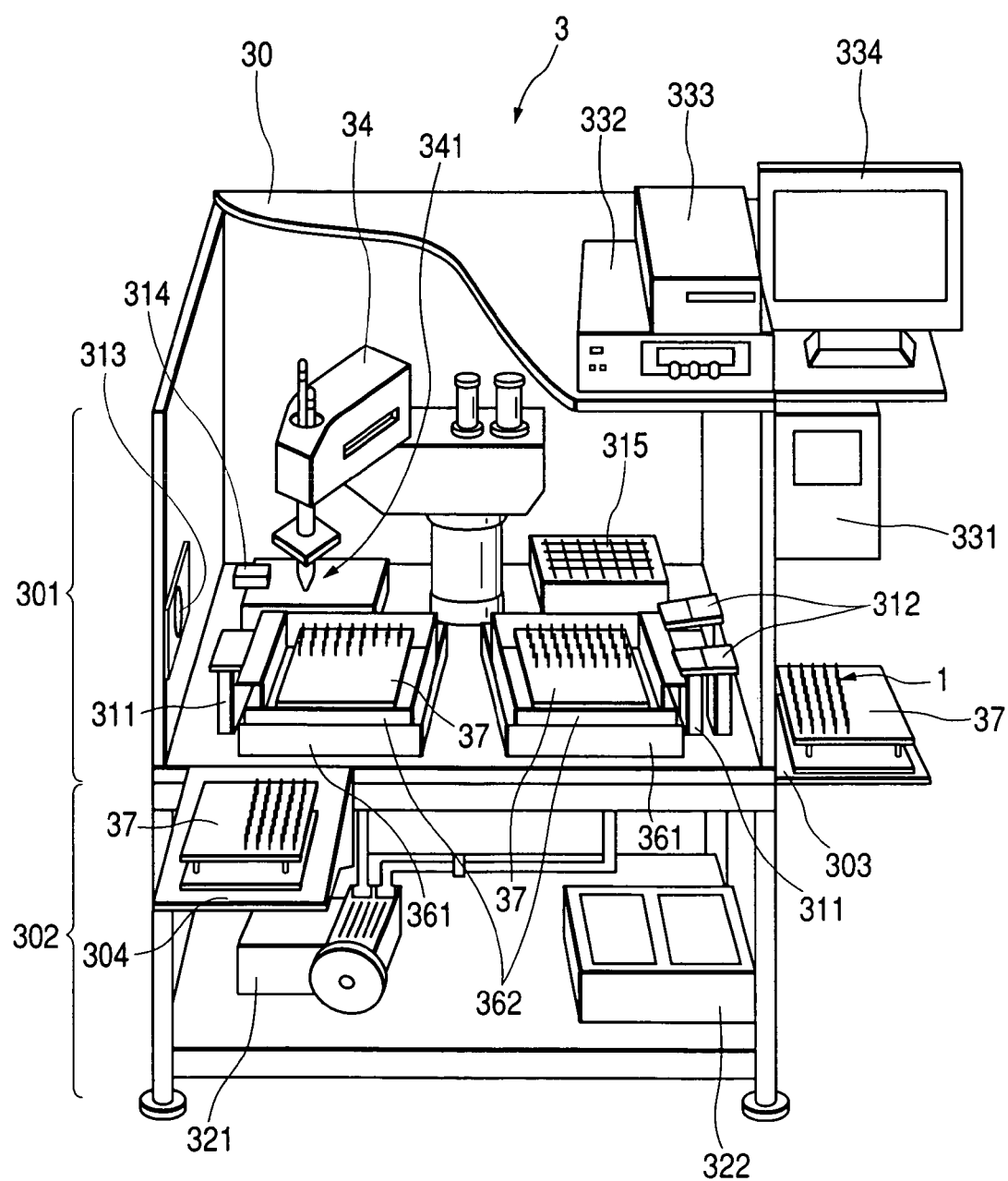
FIG. 5 is an illustration of an inspection apparatus to be used for an inspection of a multilayer gas sensing device according to a second embodiment of the present invention.

As FIG. 5 shows, an inspection apparatus, generally designated at reference numeral 3, includes a pump unit 321 and an R/B controller 322 in a lower section 302 of a housing 30, and further includes, in an upper section 301 thereof, two inspection vessels 362, a blower 312 using dried air, a discharge opening 313 for the dried air from the blower 312, a defective storage 315, a robot arm 34 with an inspection head 341, and a drier 314 for drying the inspection head 341. In the exterior of the housing 30, there are placed pallet tables 303, 304, a super insulation measuring device 332, a resistance measuring device 333, a recorder 334 and an control panel 331.

Figure 6:
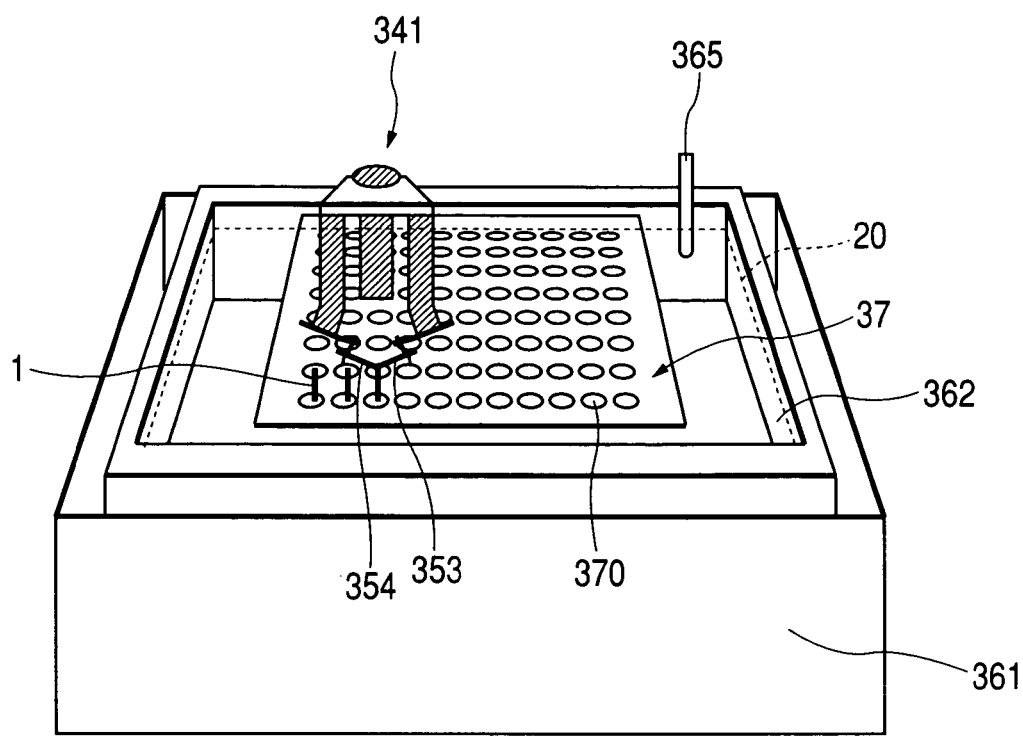
FIG. 6 is an illustration of an inspection vessel and a pallet set in the inspection vessel according to the second embodiment.
Figure 7:
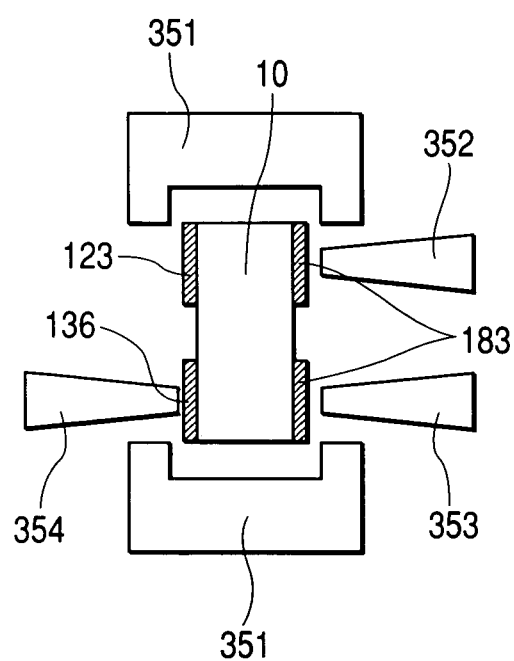
FIG. 7 is an illustration of the positional relationship among a measurement terminal, a removing chuck, and the multilayer gas sensing device according to the second embodiment.

A pallet 37 in which the multilayer gas sensing devices 1 are set as shown in FIG. 7 is located in the inspection vessel 362, and as shown in FIG. 6, in the inspection vessel 362, there are provided a liquid level sensor 365 used for maintaining the liquid level constant, and there is provided an outside vessel 361 for accommodating an excessive conductive inspection solution discharged in maintaining the liquid level of the inspection vessel 362 constant. Moreover, the pump unit 321 is provided in order to collect and re-circulate the excessive conductive inspection solution. Incidentally, only three multilayer gas sensing devices are shown in FIG. 6.

Figure 8A:
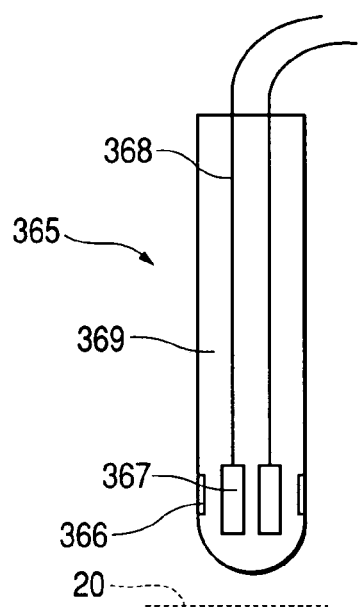
FIGS. 8A and 8B are illustrations of a construction of a liquid level sensor according to the second embodiment.
Figure 8B:
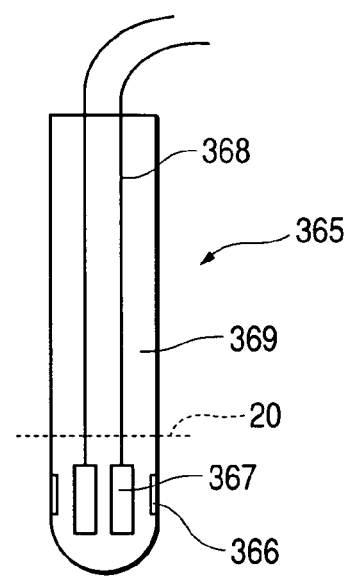

As shown in FIGS. 8A and 8B, the liquid level sensor 365 is composed of a blind-end cylindrical main body 369 having suction holes 366 in its side surfaces, a pair of electrodes 367 located in the interior of the main body 369 and lead wires 368 respectively connected to the pair of electrodes 367.

As shown in FIG. 8A, in a case in which the liquid level sensor 365 is placed above the liquid level 20, since the electrodes 367 in the main body 369 are not placed into an electrical connection state, even if a voltage is applied through the lead wires 368, not current flows.

On the other hand, as shown in FIG. 8B, when the liquid level sensor 365 is immersed therein, the conductive inspection solution comes through the suction holes 366 in the interior of the main body 369 and an electrical connection takes place between the electrodes 367, so a current flows when a voltage is applied through the lead wires 368. This signifies that the liquid level 20 rises and goes beyond a predetermined position.

The robot arm 34 equipped with the inspection head 34 is of a horizontal articulated type to be controlled by the R/B controller 322. As shown in FIG. 7, the inspection head 341 is composed of two types of measurement terminals 352, 353, 354 and a removing chuck 351 capable of holding the multilayer gas sensing devices 1 to transfer them from the pallet 37.

Of the two types of measurement terminals, the one type includes the two electrical resistance measurement terminals 352 and 353 connected to a resistance measuring device 333 for measuring an electrical resistance of the heater of the multilayer gas sensing device 1 to make a decision as to whether or not it satisfies a specification, while the other is the one insulation measurement terminal 354 connected to the super insulation measuring device 332 for conducting the inspection according to the first embodiment. The super insulation measuring device 332 has another ground terminal which is immersed in the conductive inspection solution in the inspection vessel 362 during the inspection. Although being omitted in FIG. 6, the ground terminal is fixedly secured onto an inner side surface of the inspection vessel 362. It is also acceptable that the ground terminal resides in the solution.

Figure 9A:
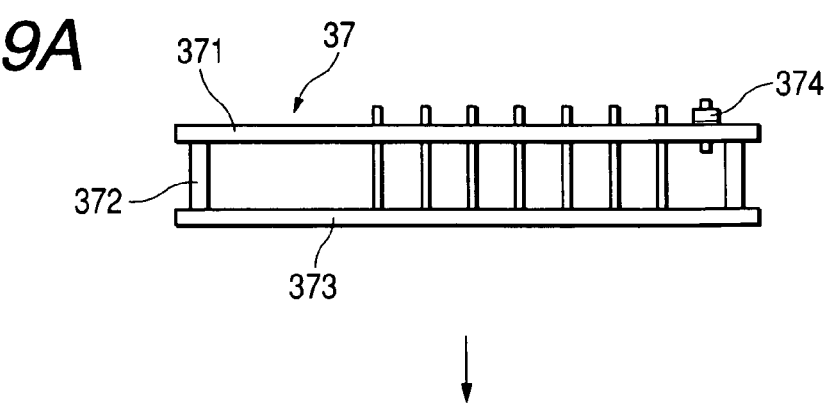
FIGS. 9A and 9B are illustrations of a pallet for setting multilayer gas sensing devices for the inspection according to the second embodiment.

As shown in FIGS. 6 and 9A, the pallet 37 is composed of an upper plate 371 having a large number of holding holes 370 for holding the multilayer gas sensing devices 1, a lower plate 373 against which the tip portions of the gas sensing devices 1 run, and columns 372 for maintaining a predetermined space between the upper and lower plates 371 and 373. Moreover, an inspection pin 374 is set in the upper plate 371 before the inspection in order to facilitate the discrimination after the inspection.

Figure 9B:
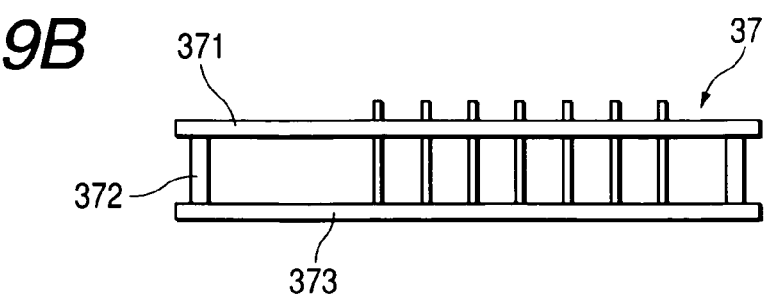
Figure 10:
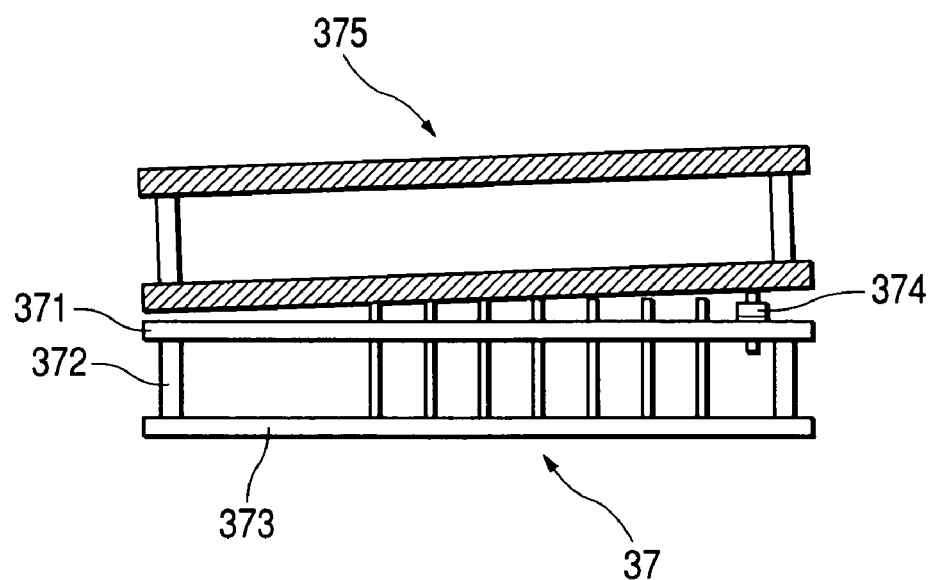
FIG. 10 is an illustration of a state in which another pallet is stacked on the pallet in which inspection pins are set.

As FIG. 10 shows, when the inspection pin 374 exists, another pallet 375 cannot be put on the pallet 37, and the discrimination is easily feasible. FIG. 9B shows a state in which the inspection pin 374 is removed therefrom. Moreover, for the pallet in which the inspection pin 374 does not exist, the apparatus is not automatically activated and the inspection does not take place. The robot arm 34 automatically removes the inspection pin 374 from the pallet after the completion of the inspection, thereby preventing the outflow (process jumping) of non-inspected products.

Secondly, a description will be given hereinbelow of an inspection procedure using the inspection apparatus 3 according to this embodiment.

First of all, an operator manually sets the multilayer gas sensing devices 1 to be inspected in the pallet 37. In this case, 100 multilayer gas sensing devices 1 can be set in one pallet 37. For the discrimination between the pallet 37 before the inspection and the pallet 37 after the inspection, the inspection pin 364 is set in the pallet 37 before the inspection. The multilayer gas sensing devices 1 are set on the pallet tables 303 and 304.

Following this, the pallet 37 is set in the inspection vessel 362.

Subsequently, when the inspection apparatus 3 is activated through the control panel 331, an automatic pallet elevator 311 puts the pallet 37 down in the inspection vessel 362 so that the multilayer gas sensing devices 1 are immersed in the conductive inspection solution until reaching a predetermined position. In the case of the multilayer gas sensing device 1 according to the first embodiment, the liquid level is adjusted to be at a position of 18 to 30 mm from the tip portions of the multilayer gas sensing devices 1. During this adjustment, the excessive conductive inspection solution is discharged to the outside vessel 361.

The inspection apparatus 3 according to this embodiment has two inspection vessels 362. This enables the inspection to be made in one inspection vessel 362 while the pallet 37 is set in the other inspection vessel 362, thus shortening the inspection time.

Moreover, in the case of an inspection apparatus equipped with a plurality of inspection vessels 362 like this embodiment, the inspection vessels 362 are individually and efficiently operable, thus eliminating the wasteful use of the inspection solution, and enhancing the degree of freedom on the design of facility (location of the inspection vessels, and the like).

Thereafter, as shown in FIG. 6, the inspection head 341 is shifted to just above the multilayer gas sensing device 1 to be inspected and the electrical resistance measurement terminals 352 and 353 are first brought into contact with the heater terminal 183 of the multilayer gas sensing device 1. This enables the electrical resistance of the heater to be measured to detect the defectives one the heater. Moreover, the multilayer gas sensing device 1 which does not satisfy the specification is carried away to the defective storage 315 by means of the removing chuck 351.

Incidentally, in the case of the poor contact of the electrical resistance measurement terminals 352 and 353 and if the electrical resistance measurement terminals 352 and 353 come into contact with the reference side external terminal 136 located surface of the multilayer gas sensing device 1, the resistance value takes the infinity and the measurement becomes impossible. In this case, this multilayer gas sensing device 1 is likewise carried away to the defective storage 315.

Following this, the super insulation measurement terminal 354 is brought into contact with the reference side external terminal 136 electrically connected to the reference electrode of the multilayer gas sensing device 1 and a ground terminal (not shown) is immersed in the conductive inspection solution and, in this state, a voltage of 500±10 V is applied to carry out the super insulation measurement. In this measurement, when the flowing current exceeds 5 $\mu$A, that multilayer gas sensing device 1 is regarded as a defective product and carried away to the defective storage 315.

Thus, the multilayer gas sensing devices 1 set in the pallet 37 are checked one by one and all the defective products are finally removed from the interior of the pallet 37.

When only the non-defective products remain in the pallet 37, the inspection apparatus 3 is operated through the control panel 331 to fall into a stopped condition, and the operator removes the after-inspected pallet 37 from the inspection vessel 362 and places a non-inspected pallet 37 newly.

During the aforesaid inspection, through the use of the dried air blower 312, the dried air having a humidity below 30% and a temperature below the room temperature is directed at the discharge opening 313 through a portion above the pallet 37. Moreover, the inspection head 341 is dried by the dried air from the drier 314 whenever each multilayer gas sensing device 1 is inspected, thereby preventing the error stemming from the wetness. Still moreover, the measurement results in the resistance measuring device 333 and the super insulation measuring device 332 are fed to the computer-based recorder 334, installed in the exterior of the inspection apparatus 3, to be recorded therein.

Thus, the employment of the apparatus according to this embodiment enables the inspection of a large number of multilayer gas sensing devices according to the inspection method according to the first embodiment.

(Third Embodiment)

Figure 11:
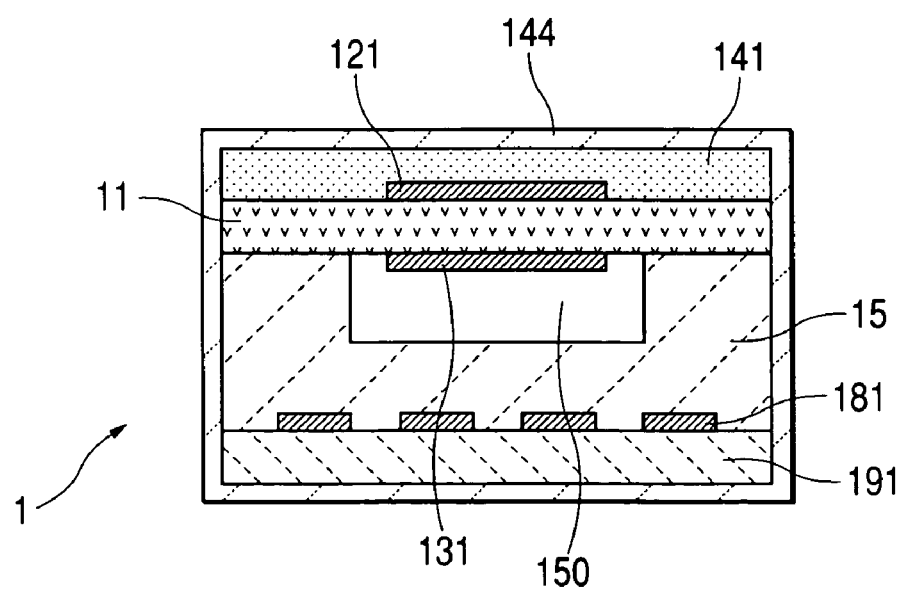
FIG. 11 is an illustration of a construction of a multilayer gas sensing device equipped with a dense protective layer which is capable of generally cutting off gases and which is provided so as to surround the entire circumferential surface of the multilayer gas sensing device.

As shown in FIG. 11, a multilayer gas sensing device 1 related to a third embodiment of the present invention is constructed such that the entire circumference of the multilayer gas sensing device 1 is covered with the dense protective layer.

That is, the multilayer gas sensing device 1 according to this embodiment is composed of a solid electrolyte plate 11 having a measured gas side electrode 121 exposed to a measured gas and a reference electrode 131 confronting a reference gas chamber 150 and exposed to a reference gas, a spacer 15 for defining the reference gas chamber 150 and a heater substrate 191 equipped with a heating element 181.

The measured gas side electrode 121 is covered with a porous diffusion resistance layer 141, and a dense protective layer 144 capable of cutting off gases is provided to surround the entire circumference of the multilayer gas sensing device 1.

The other detailed construction is like that described in the first embodiment, and when the inspection according to the first embodiment is conducted with respect to the multilayer gas sensing device in this embodiment, the like effects are obtainable.

It should be understood that the present invention is not limited to the above-described embodiments, and that it is intended to cover all changes and modifications of the embodiments of the invention herein which do not constitute departures from the spirit and scope of the invention.

What is claimed is:

1. A method of inspecting a multilayer gas sensing device which comprises a sensor cell including a solid electrolyte plate, a measured gas side electrode placed on a surface of said solid electrolyte plate to be exposed to a measured gas and a reference electrode placed on a surface of said solid electrolyte plate to be exposed to a reference gas, said method comprising the steps of:

immersing said multilayer gas sensing device in a conductive inspection solution;

placing said reference electrode into non-contact condition with said conductive inspection solution;

applying a voltage between said conductive inspection solution and said reference electrode to measure a current flowing between said conductive inspection solution and said reference electrode; and making a decision as to whether or not insulation is kept between said conductive inspection solution and said reference electrode.

2. The method according to claim 1, wherein, in the step of applying said voltage between said conductive inspection solution and said reference electrode, said voltage is applied between a reference side external terminal and said conductive inspection solution, the reference side external terminal being electrically connected to said reference electrode, formed in an exposed state outside said multilayer gas sensing device, and arranged to be separated from said conductive inspection solution.

3. The method according to claim 1, wherein said voltage to be applied between said conductive inspection solution and said reference electrode is in a range from 250V to 1000V.

4. The method according to claim 1, wherein, when a current flowing between said conductive inspection solution and said reference electrode in response to the voltage application therebetween is below 5 $\mu$A, said multilayer gas sensing device is decided to be a non-defective product.

5. The method according to claim 1, wherein said conductive inspection solution is an ethanol.

* * * * *

UNITED STATES PATENT AND TRADEMARK OFFICE
CERTIFICATE OF CORRECTION

PATENT NO. : 7,013,701 B2
APPLICATION NO. : 10/730884
DATED : March 21, 2006
INVENTOR(S) : Kawashima It is certified that error appears in the above-identified patent and that said Letters Patent is hereby corrected as shown below:

On the Title Page;

"(55) INSPECTION METHOD OF MULTILAYER
GAS SENSING DEVICE"

should be

--(55) INSPECTION METHOD FOR MULTILAYER
GAS SENSING DEVICE--.

In Columns 11 – 12, claims 1 and 2 should be as follows:

1. A method of inspecting a multilayer gas sensing device which comprises a sensor cell including a solid electrolyte plate, a measured gas side electrode placed on a surface of said solid electrolyte plate to be exposed to a measured gas and a reference electrode placed on a surface of said solid electrolyte plate to be exposed to a reference gas, with said measured gas side electrode being coated with a porous diffusion resistance layer in a stacked condition and said diffusion resistance layer being further coated with a dense protective layer in a stacked condition, said method comprising the steps of:
    immersing said multilayer gas sensing device in a conductive inspection solution;
    placing said reference electrode into non-contact condition with said conductive inspection solution;
    applying a voltage between said conductive inspection solution and said reference electrode to measure a current flowing between said conductive inspection solution and said reference electrode; and
    making a decision as to whether or not insulation is kept between said conductive inspection solution and said reference electrode.

UNITED STATES PATENT AND TRADEMARK OFFICE
CERTIFICATE OF CORRECTION

PATENT NO. : 7,013,701 B2
APPLICATION NO. : 10/730884
DATED : March 21, 2006
INVENTOR(S) : Kawashima It is certified that error appears in the above-identified patent and that said Letters Patent is hereby corrected as shown below:

2. The method according to claim 1, wherein, for applying said voltage between said conductive inspection solution and said reference electrode, said voltage is applied between a reference side external terminal, which is electrically connected to said reference electrode and formed in an exposed state in the exterior of said multilayer gas sensing device and which does not come into contact with said conductive inspection solution, and said conductive inspection solution.

Signed and Sealed this

Twenty-ninth Day of August, 2006

JON W. DUDAS
*Director of the United States Patent and Trademark Office*